United States Patent [19]

van Dommelen et al.

[11] Patent Number: 5,321,126

[45] Date of Patent: Jun. 14, 1994

[54] METHOD OF PREPARING A FIBRINOGEN CONCENTRATE FROM BLOOD PLASMA

[75] Inventors: Frederik S. van Dommelen, Apeldoorn; Gerrit Wijngaards, Driebergen-Rijsenburg, both of Netherlands

[73] Assignee: Harimex-Ligos B.V., Loenen, Netherlands

[21] Appl. No.: 913,750

[22] Filed: Jul. 17, 1992

Related U.S. Application Data

[63] Continuation of Ser. No. 638,990, Jan. 10, 1991, abandoned.

[30] Foreign Application Priority Data

Jan. 15, 1990 [NL] Netherlands ............... 9000090

[51] Int. Cl.$^5$ ............................... A61K 35/14
[52] U.S. Cl. ................... 530/382; 530/380; 424/530
[58] Field of Search .......... 530/382, 380, 383; 424/530; 210/774, 782, 787, 905

[56] References Cited

U.S. PATENT DOCUMENTS

| | | | |
|---|---|---|---|
| 2,710,294 | 6/1955 | Gerlaugh et al. | 530/350 |
| 3,297,532 | 1/1967 | Jones | 530/382 |
| 4,141,887 | 2/1979 | Seufert | 530/350 |
| 4,486,341 | 12/1984 | Chang | 530/350 |
| 4,627,879 | 12/1986 | Rose et al. | 106/124 |

OTHER PUBLICATIONS

Dresdale et al. (1985) Surgery 97(6): 750–755, 1985.
Spotnitz et al. (1987), The American Surgeon 53(8): 460–462.

Primary Examiner—Michael G. Wityshyn
Assistant Examiner—C. Sayala
Attorney, Agent, or Firm—Cushman, Darby & Cushman

[57] ABSTRACT

A method of preparing fibrinogen concentrate from blood plasma by cooling said plasma from a temperature above 0° C. to a first temperature between −10° C. and −40° C., thawing the solid material thus obtained to a temperature near the freezing point of water and subsequently physically separating the solid matter and the liquid main fraction of the plasma, viz. water, whereby the thawing is effected in steps from the first temperature to a conditioning temperature between −5° C. and −1° C., after which the size of the solid material is reduced and the reduced material is brought to a temperature at which the main fraction of the plasma, viz. water, becomes liquid and the solubility of fibrinogen in said fluid is as low as possible, after which fluid is separated from the fibrinogen concentrate. The invention also relates to a device for carrying out this method.

12 Claims, 1 Drawing Sheet

METHOD OF PREPARING A FIBRINOGEN CONCENTRATE FROM BLOOD PLASMA

This is a continuation of application Ser. No. 07/638,990, filed on Jan. 10, 1991, now abandoned.

The invention relates to a method of preparing fibrinogen concentrate from blood plasma by cooling said plasma from a temperature above 0° C. to a first temperature between −10° C. and −40° C., thawing the solid material thus obtained to a temperature near the freezing point of water and subsequently physically separating the solid matter and the liquid main fraction of the plasma, viz. water. The invention furthermore relates to a method of preparing fibrinogen from the fibrinogen concentrate thus obtained and to a device for preparing said fibrinogen concentrate.

From an article by A. M. Cucuianu et al, published in Rev. Chir. Oncol. Radiol ORL Oftamol Stomatol SER OT-Rino-Laringol, 33 (2), 1988, pages 81–88, entitled: "Preliminary data on the preparation of a fibrin glue from the patient's plasma and its utilization in ORL Surgery" a method is known for preparing fibrinogen by cooling citrate-containing plasma to −20° C., then slowly thawing, to a temperature between 0° C. and +4° C., and cold-centrifuging said plasma. However the efficiency is low when this method is used, and can be enhanced considerably by using a method according to the invention. From an article by W. D. Spotnitz et al, published in AM Surg. 53 (8), 1987, pages 460–462, entitled: "Fibrin glue from stored human plasma, an inexpensive and efficient method for local blood bank preparation", a method of separating fibrinogen from blood plasma is known, whereby the emphasis is in particular put on preventing therapeutically undesirably factors, such as hepatitis, in the final product obtained. This method is only used on a small scale and it only discloses the fact that frozen fresh plasma is used.

From British patent application 2 096 147 a process is known for separating a precipitate from blood that especially comprises factor VIII being a substance used in haemostatis therapy. According to this method frozen plasma at a temperature of about −10° C. is heated to a temperature of 0°–1° C. under circulation in an apparatus specially developed for this method, so that particles can be obtained, comprising factor VIII having a diameter of about 0.2 cm. This patent application is especially directed to the specific apparatus for thawing. From U.S. Pat. No. 4,278,592 a process and apparatus are known to prepare sterile filtered blood clotting products from fibrinogen with an enrichment of Factor 1. In order to do so blood is extracted from a donor, plasma is separated from the blood and the plasma is frozen at a temperature below about −22° C. Then the blood plasma is thawed in order to produce a cyro-precipitate, drawing off the plasma present above the cyro-precipitate and fibrinogen is produced from said plasma after which the fibrinogen is dissolved in a buffer and the fibrinogen dissolved in the buffer is filtrated. This process is different from the process according to the invention with respect to the aim as well as concerning the process to be carried out, because the process according to the invention is directed to the commercial production of fibrinogen. From U.S. Pat. No. 2,543,808 (1951) a method is known for preparing fibrinogen by melting frozen plasma and to recover fibrinogen at about 0° C., after which the obtained product is washed with 3–6 portions of dilute saline at about 0° C. and the remaining fibrinogen then is dissolved in a minimal quantity of dilute saline at a temperature between 15° and 40° C., after which the undissolved material is separated. In this method chemicals have been added to fibrinogen, which is undesired for the production of food.

Fibrinogen is a protein which is soluble in the blood plasma, which protein is converted, under the influence of trombine, into fibrine, causing the blood to clot. U.S. Pat. No. 4,741,906 discloses a method wherein scraps of meat are attached together by means of a fibrinogen solution, so that larger chunks of meat are formed. This method can in particular be used in the meat processing industry. This industrial application and the further applications to be expected have made it necessary to produce fibrinogen on a large scale, on an industrial scale, therefore.

At the moment fibrinogen is being prepared on a small scale by separating it from blood plasma by chemical means, which are added to the blood plasma, so that the proteins present therein are precipitated and then recovered. In the food industry, however, it is undesirable to work with starting materials to which chemicals, such as extracting agents or solvents, have been added, or which have undergone treatment at elevated temperatures above 50° C., as a result of which the effect of the fibrinogen deteriorates. Therefore it has been attempted to achieve a method of preparing fibrinogen without additives or auxiliary materials being added, or without an elevated temperature being employed.

Now it has become possible to separate, on an industrial scale, fibrinogen concentrate from blood plasma by means of physical separation, whereby a high efficiency is achieved. The experiments carried out showed that in particular the step between freezing, at a first temperature of about −20° C., and separating fibrinogen, for example by centrifuging at a temperature of about 0° C., is important. This important step will be referred to as "conditioning" hereinafter.

The method according to the invention is characterized in that the thawing is effected in steps from the first temperature to a conditioning temperature between −5° C. and −1° C., after which the size of the solid material is reduced and the thus reduced material is brought to such a temperature that the main fraction of the plasma, viz. water, becomes liquid and the solubility of fibrinogen in said fluid is as low as possible, after which water is separated from the fibrinogen concentrate. The temperature to which the thus reduced material is raised, so that the larger part of the material is liquid, lies preferably between −2° C. and 0° C. This temperature must be achieved by a gradual temperature elevation, whereby it should be attempted to avoid that the material is locally overheated to a temperature which is considerably higher than 0° C., this gradual elevation of the temperature is preferably achieved in a recirculation system incorporating a heat exchanger, whereby the weight ratio between fresh material and recirculated material is 1:1.5–5, so that the material is heated in the recirculation system to the temperature at which the fibrinogen concentrate can be separated from the liquid, preferably by centrifuging, viz. to a temperature between −2° C. and 0° C.

It may be assumed, although this does not constitute a limitation of the invention, that as a result of said conditioning the protein to be recovered, fibrinogen, is less soluble in the liquid phase of the blood plasma than might be expected at the temperature at which the separation, such as centrifuging the fibrinogen concentrate, is eventually carried out.

The invention furthermore relates to a device which is used for carrying this method.

BRIEF DESCRIPTION OF THE DRAWINGS

The invention will be explained in more detail in the following description, whereby reference is made to the appended drawing, in which.

DETAILED DESCRIPTION

Figure 1A:
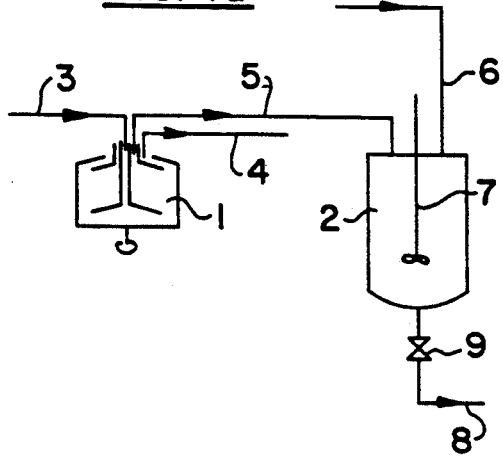
FIG. 1a schematically shows apparatus for the first step of separating blood plasma from blood.
Figure 1B:
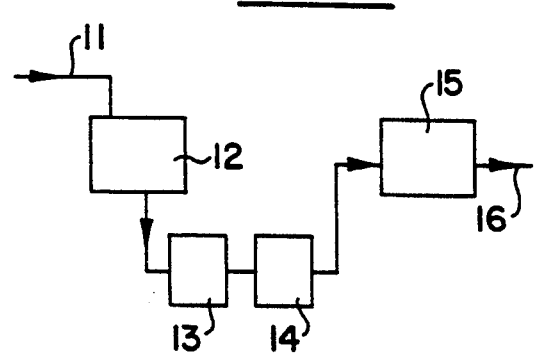
FIG. 1b schematically shows apparatus for the second step of freezing and conditioning the fibrinogen containing plasma.
Figure 1C:
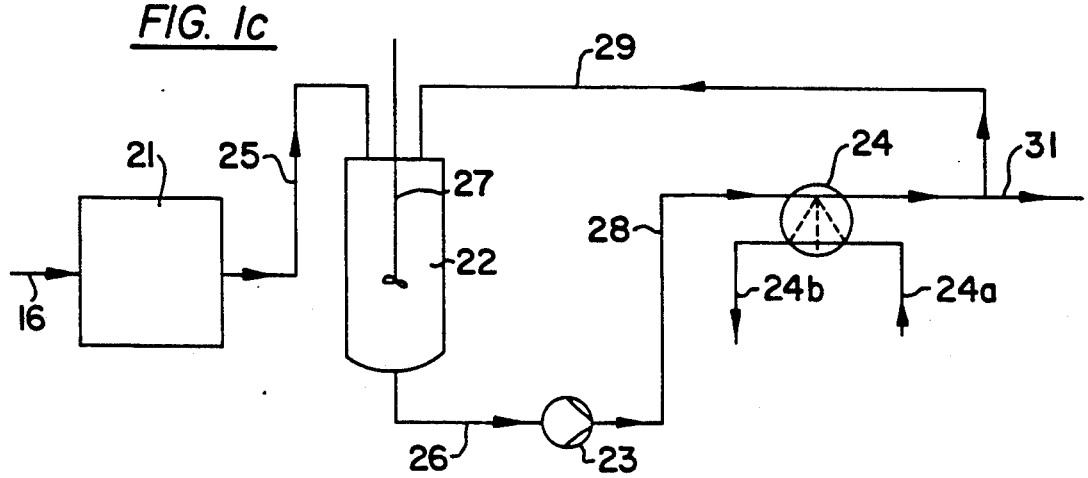
FIG. 1c schematically shows apparatus for the third step of reducing the conditioned plasma.
Figure 1D:
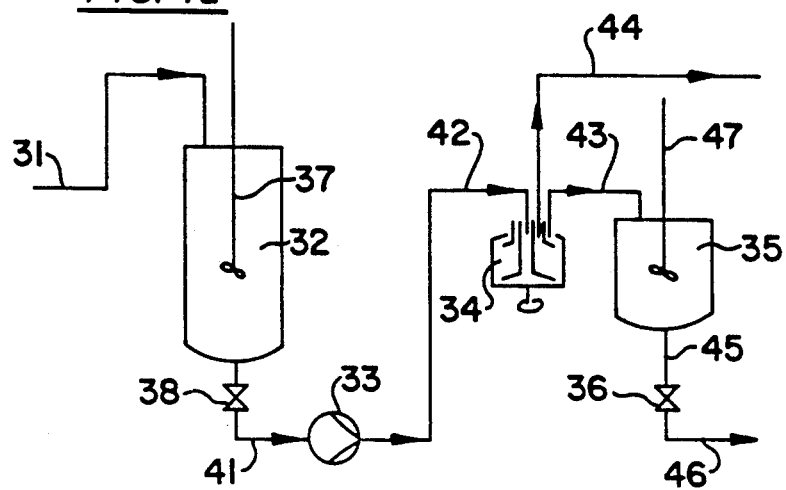
FIG. 1d schematically shows apparatus for the fourth step of separating plasma and fibrinogen.

FIG. 1 illustrates in a first step 1-a), indicated by reference numbers 1-9, the separation of blood plasma from blood, which step does not form part of the subject matter of the present invention, its only purpose is to aid in describing the process as completely as possible.

Via the line 3 blood, preferably acquired from slaughter cattle, with a temperature of about 4° C. is supplied to the centrifuge 1. After centrifuging thickened blood is discharged via the line 4, and plasma having a pH of 7.7 at a temperature of about 4° C. is supplied, via the line 5, to a plasma storage vessel 2 provided with a stirrer 7, in which storage vessel 2 the pH of the plasma is adjusted to a value of about 8.5, by adding NaOH, as a 30% aqueous solution, to the storage vessel 2 via the line 6. From the vessel 2 plasma having a pH of about 8.5 and a temperature of about 4° C. is discharged via the line 8, said discharge being adjustable by means of the valve 9.

In a second step 1-b) the fibrinogen-containing plasma obtained in the first step is further processed by freezing and conditioning. For this purpose the plasma obtained from the first step is supplied, via the line 11, to a freezing plant (plate freezer) 12. In said freezing plant 12 the plasma is frozen to a temperature between −10° C. and −40° C., preferably at a temperature of about −20° C. The blocks of plasma thus obtained can be sawed into discs having a size of 9×20 cm, with a thickness of about 7-9 mm. Said discs are formed by means of e.g. a saw 13. Then the discs may be conditioned. It is also possible, however, to store a buffer stock of discs in a cold storage room 14, at a temperature of about −20° C., whereby the storing in the cold storage room is preferably done in polyethylene wrapping material. Furthermore it is possible to store several discs in one package, e.g. three discs, so that eventually large discs having a size of 27-20 cm and having a thickness of 7-9 mm are stored in the cold storage room 14. Also the blocks of plasma, obtained in the freezing plant 12, may be directly transferred to the conditioning room 15. It will be clear that in the case of discs the heat transfer in the room 15 can be controlled more easily that when blocks having much larger dimensions than the discs are used.

After possible storage in a cold storage room 14, at a temperature of about −20° C., the blocks or discs are stripped of their packing material, if necessary, and supplied to a conditioning room 15. In said conditioning room 15 the material is heated, from a temperature such as prevails in the cold storage room 14 or in the freezing plant 12, preferably a temperature of about −20° C., to a post-conditioning temperature viz. a temperature between −5° C. and −1° C. With said conditioning the final temperature and the time during which said conditioning is carried out are important. The temperature of the discs must be increased from about −20° C. to a temperature just under the freezing point of water, in order to reduce the size of the discs in the subsequent step. Discs having a temperature of about −20° C. are very difficult to reduce, said reduction in size being necessary in order to be able to carry out the further physical separation between fibrinogen concentrate and plasma fluid. From the experiments carried out it has become apparent that the manner in which conditioning is carried out is very important for the fibrinogen-recovering efficiency. This also appears from the experiments mentioned hereafter. With regard to the conditioning time it applies that a period of more than 24 hours hardly improves the efficiency, and that a period of 0.5 hour and longer provides a substantially improved efficiency. For this reason conditioning is preferably carried out for 0.5-48 hours, more preferably for 2-24 hours.

After the discs or blocks have been conditioned in the conditioning room 15, the discs are supplied in a third step 1-c) to the devilling machine 21, at a temperature between −5° C. and −1° C., preferably at a temperature of about −2° C., said devilling machine being an example of an apparatus for further reducing the size of the discs. According to a preferred method the reduced material is then supplied, via the line 25, to the recirculation vessel 22 provided with a stirrer 27. The recirculation system consists of the recirculation vessel 22, the pump 23, the heat exchanger 24 and the lines in question, such as indicated in the drawing. Said heat exchanger 24 is on the one hand fed, via the line 28, with pumpable fibrinogen-containing plasma having a temperature of about −2° C., and on the other hand one supplies water to the heat exchanger 24, whereby the temperature at the inlet 24a is the ambient temperature, or slightly higher, viz. about 30° C., and at the outlet 24b water is discharged having a temperature which is about 10° C. lower, viz. about 20° C. On an average the fibrinogen-containing plasma will pass through the cycle 3-4 times and then be discharged via the line 31.

The fourth step 1-d) of the method is in principle carried out in the centrifuge 34. For this purpose the fibrinogen-containing plasma obtained from the third step, which has a temperature of about 0° C., preferably slightly below 0° C., is supplied as a liquid with solid fibrinogen present therein, via the line 31, to the receiving vessel 32 provided with a stirrer 37, so that a quantity which can be adjusted via the valve 38, is supplied to the centrifuge 34 via the line 41, the pump 33 and the line 42. Residual plasma is on the one hand discharged from the centrifuge and on the other hand the fibrinogen concentrate is supplied to the storage vessel 35 with stirrer 47, said fibrinogen concentrate being homogenized and discharged, via the line 45, the control valve 36 and the line 46, and being packed and frozen in order to be stored until being used. If required powdered fibrinogen can be recovered from said concentrate.

The invention will be further explained on basis of the following examples.

EXAMPLE I

Using apparatus as illustrated in FIG. 1, blood acquired from cattle was separated into thickened blood and plasma, whereby the blood was first cooled to a temperature of 4° C., after which said separation took place by means of a centrifuge, so that plasma having a pH of 7.7 was obtained, as well as thickened blood, which was discharged. The pH of the plasma was adjusted to 8.5 by means of the 30% NaOH and the plasma was supplied to the plate freezer 12 at a temperature of 4° C., in which plate freezer the plasma was cooled to −20° C. The frozen blocks of plasma thus obtained are cut into discs being dimensioned 9×20 cm and having a thickness of 8 mm.

These discs were conditioned in a conditioning room 15 for 24 hours, at a temperature of −2° C. Then the conditioned discs were supplied, at a temperature of −2° C., to a disc-reducing installation, for which purpose a devilling machine was employed. The discharge from said devilling machine 21 amounted to 800 kg/h of in size reduced fibrinogen-containing plasma having a temperature of −2° C. Said reduced material was supplied to a circulating vessel 22, in which it was mixed with 2200 kg/h of recirculated material obtained from the heat exchanger 24, said material having a temperature of 0° C. Thus 3000 kg/h of fibrinogen-containing plasma having a temperature of −1° C. was discharged from the circulation vessel 22. The heat exchanger 24, being a heating medium, was fed with 6500 kg/h of water having a temperature of 30° C., while the same quantity of water, having a temperature of 20° C., was discharged via the line 24b.

Via the line 31 800 kg/h of fibrinogen-containing plasma having a temperature of 0° C. was supplied to the receiving vessel 32, and supplied to the centrifuge 34 by means of the pump 33, from which centrifuge 70 kg/h of fibrinogen concentrate was obtained, which was supplied to the storage vessel 35, and on the other hand 730 kg/h of residual plasma was removed from the centrifuge via the line 44. From the storage vessel 35 the desired final product, viz. fibrinogen concentrate, was discharged via the line 46, and finally frozen and packed.

The fibrinogen recovering efficiency amounted to 73.6% with this embodiment.

EXAMPLES II-V AND COMPARATIVE EXAMPLE

The methods according to examples II-IV were carried out in the same manner as indicated in example I; in the examples II and III, however, conditioning took place at a temperature of −2° C., for a period of 2 hours and 30 minutes respectively. In that case the efficiency was 50.2% and 16.6%, respectively.

In example IV the conditioning time was minimized, which implies that the temperature of the fibrinogen-containing plasma was raised from −20° C. to −2° C., and as soon as this temperature was reached the material was reduced. With a conditioning time of 0 hours the efficiency was 10.8%.

In the comparative example conditioning was carried out for 18 hours at −10° C., the efficiency was 5.1%.

From these data it becomes apparent that conditioning for 24 hours at −2° C. results in a considerably increased efficiency compared with the situation in which no conditioning is carried out, since the efficiency is increased from 10.8% to 73.6%.

Conditioning at a temperature of −10° C. does not give any result at all, not even when this is done for 18 hours. Further tests have shown that conditioning at a temperature between −2° C. and −5° C. gives comparable results.

We claim:

1. A method of preparing fibrinogen concentrate from blood plasma comprising the steps of:
   cooling plasma from a temperature above 0° C. to a first temperature between about −10° C. and −40° C. to obtain a solid material;
   bringing the plasma to a conditioning temperature between −5° C. and −1° C., holding the plasma at the conditioning temperature for 0.5 to 48 hours, after which the size of the solid material is reduced, and increasing the temperature of the solid material so that the main fraction of the plasma, viz. water, becomes liquid, and thereafter separating the liquid from the fibrinogen concentrate.

2. A method according to claim 1, wherein fibrinogen concentrate is separated from the liquid main fraction of plasma by centrifuging at a temperature of 0° C.

3. A method according to claim 1, wherein after conditioning the temperature is raised to a value between −2° C. and 0° C. by stirring the plasma and mixing it in a recirculation system including a heat exchanger whereby the weight ratio of the plasma to recirculated material amounts to 1:1.5-5.

4. A method according to claim 3, wherein the fibrinogen concentrate is separated from the liquid main fraction of plasma by centrifuging at a temperature of 0° C.

5. A method according to claim 3, wherein after conditioning and reducing the solid fibrinogen concentrate recirculation takes place in the heat exchanger while heating to a discharge temperature between −0.5° C. and 0° C.

6. A method according to claim 5, wherein the fibrinogen concentrate is separated from the liquid main fraction of plasma by centrifuging at a temperature of 0° C.

7. A method according to claim 3, wherein a recirculation ratio is 1 part of conditioned fresh material to 2-4 parts of recirculated material.

8. A method according to claim 3, wherein said temperature is raised in the heat exchanger, using water at ambient temperature.

9. A method according to claim 1, wherein said conditioning temperature is between −5° C. and −2° C.

10. A method according to claim 9, wherein the plasma is held at the said conditioning temperature for 2-24 hours.

11. A method according to claim 9, wherein said conditioning temperature is between −3° C. and −1.5° C.

12. A method of preparing fibrinogen from a water-containing fibrinogen concentrate by removing water from said concentrate and recovering solid fibrinogen, wherein a fibrinogen concentrate prepared in accordance with the method of claim 1 is used.

* * * * *